United States Patent
Maggi et al.

(10) Patent No.: US 10,517,828 B2
(45) Date of Patent: *Dec. 31, 2019

(54) COMPOSITION COMPRISING AT LEAST ONE DRY POWDER OBTAINED BY SPRAY DRYING TO INCREASE THE STABILITY OF THE FORMULATION

(71) Applicant: ERATECH S.R.L., Bresso (MI) (IT)

(72) Inventors: Loretta Maggi, Piacenza (IT); Giovanni Caponetti, Piacenza (IT); Heike Butti, Piacenza (IT); Cristina Veneziani, Castel San Giovanni (IT); Laura Zanellotti, Piacenza (IT)

(73) Assignee: ZAMBON S.P.A., Bresson (MI) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 15/517,689

(22) PCT Filed: Oct. 7, 2015

(86) PCT No.: PCT/EP2015/073188
§ 371 (c)(1),
(2) Date: Apr. 7, 2017

(87) PCT Pub. No.: WO2016/055544
PCT Pub. Date: Apr. 14, 2016

(65) Prior Publication Data
US 2017/0333349 A1    Nov. 23, 2017

(30) Foreign Application Priority Data
Oct. 8, 2014  (IT) .............................. MI2014A1761

(51) Int. Cl.
*A61K 9/00*     (2006.01)
*A61K 31/58*    (2006.01)
*A61K 31/439*   (2006.01)
*A61K 9/16*     (2006.01)
*A61K 31/167*   (2006.01)

(52) U.S. Cl.
CPC .......... *A61K 9/1623* (2013.01); *A61K 9/0075* (2013.01); *A61K 9/1617* (2013.01); *A61K 31/167* (2013.01); *A61K 31/439* (2013.01); *A61K 31/58* (2013.01)

(58) Field of Classification Search
None
See application file for complete search history.

(56) References Cited

U.S. PATENT DOCUMENTS

2008/0226736 A1* 9/2008 Caponetti ............ A61K 9/0075
424/489

FOREIGN PATENT DOCUMENTS

| EP | 2682099       | * | 7/2013 |
|----|---------------|---|--------|
| EP | 2 682 099 A2  |   | 1/2014 |
| WO | WO-00/33789 A2|   | 6/2000 |
| WO | WO-02/00197 A1|   | 1/2002 |
| WO | WO-03/024396 A2|  | 3/2003 |
| WO | WO-2007/045689 A2| | 4/2007 |
| WO | WO-2013/110632 A1| | 8/2013 |

* cited by examiner

*Primary Examiner* — Robert A Wax
*Assistant Examiner* — Danah Al-Awadi
(74) *Attorney, Agent, or Firm* — Polsinelli PC

(57) ABSTRACT

The present invention relates to inhalation formulations of drugs in the form of dry powder for inhalation administration deliverable as such with an inhaler and provided with high deliverability, respirability and stability. In particular, the invention relates to a pharmaceutical composition for inhalation use in powder form comprising a first powder comprising at least a powder (a1) comprising an active agent or a pharmaceutically acceptable salt thereof, in an amount greater than 1% by weight of the powder, leucine in an amount from 5 to 70% by weight of said powder, a sugar in an amount from 20 to 90% by weight of the powder;

and a second powder comprising a mixture of a first lactose which has an X50 from 35 to 75 µm, with a second lactose which has an X50 from 1.5 to 10 µm, the content of the first and second lactose in the mixture are respectively from 85% to 96% and from 4% to 15%. The ratio by weight between the first powder and the second powder is from 1/5 to 1/100, and the composition has a fine particle fraction (FPF) greater than 60% and a delivered fraction (DF) greater than 85%.

20 Claims, No Drawings

COMPOSITION COMPRISING AT LEAST ONE DRY POWDER OBTAINED BY SPRAY DRYING TO INCREASE THE STABILITY OF THE FORMULATION

CROSS REFERENCE TO RELATED APPLICATIONS

This application is a National Phase filing under 35 U.S.C. § 371 of PCT/EP2015/073188 filed on Oct. 7, 2015; and this application claims priority to Application No. MI2014A001761 filed in Italy on Oct. 8, 2014 under 35 U.S.C. § 119. The entire contents of each application are hereby incorporated by reference.

The present invention relates to inhalation formulations of drugs in the form of dry powder for inhalation administration deliverable as such with an inhaler and provided with high deliverability, respirability and stability.

Inhalation therapy with aerosol preparations is used to administer active agents to the respiratory tract, in the mucosal, tracheal and bronchial regions. The term aerosol describes a preparation consisting of particles or fine droplets carried by a gas (usually air) to the site of therapeutic action. When the site of therapeutic action involves the pulmonary alveoli and small bronchi, the drug must be dispersed in the form of droplets or particles with an aerodynamic diameter of less than 5.0 μm.

When the target is the pharyngeal region, larger particles are more appropriate.

Conditions suitable for these treatments are represented by bronchospasm, inflammation, mucosal edema, pulmonary infections and the like.

Currently, administration of drugs in the deep lung region is obtained through inhalation devices such as:
- nebulizers, in which the drug is dissolved or dispersed in the form of suspension and carried to the lung as nebulized droplets;
- powder inhalers, capable of delivering the drug present in the inhaler as dry micronized particles; or
- pressurized inhalers, through which the drug—again in the form of droplets of solution or suspension—is carried to the deep lung region by an inert gas expanded rapidly in air by a pressurized canister.

In all these cases, technological problems have been encountered in the development of effective products that still limit the administration of drugs by inhalation.

From a clinical point of view, an ideal inhalation product should allow different administration methods to be used by the patient, since the inhalers described are generally suitable for different types of patients and administration conditions. In general, nebulizer therapy is prevalently used by elderly or pediatric patients, while therapy with dry powder or pressurized inhalers is more suitable for adults. However, the use of nebulizers is currently still considered effective, since the patient inhales the drug under rest conditions and without using forced inhalation, which is instead required for an inhalation powder. Instead, in the case of a pressurized inhaler, the product must be taken coordinating inspiration with activation of the device, to prevent the delivered particles from impacting on the bottom of the throat and failing to reach the deep lung.

For these reasons, the inhalation formulations used in these three types of inhalation devices are generally essentially very different from one another.

In the case of products for nebulizers, formulations are substantially constituted by solutions or suspensions containing as excipient salts, surfactants and preservatives to ensure isotonicity of the preparation, homogeneity of the particle size distribution in case of suspensions, and protection against microbial contamination.

In the case of pressurized preparations, the composition usually contains surfactants, propellants and co-solvents. In inhalation formulations in powder form, the excipients essentially consist of lactose with different particle size, used as diluent.

Some formulation or stability constraints in some cases have limited industrial development of inhalation products and, apart from corticosteroids, which exist substantially in all inhalation forms, in some bronchodilator and anti-cholinergic active agents some forms of administration are not available on the market. These limitations are particularly important since current respiratory therapy makes use of combinations of drugs of different kinds as the most effective technique and, in this regard, it has been possible to develop only a small number of corticosteroid-bronchodilator combinations, prevalently in the form of inhalation powder.

With regard to nebulized forms, the patient is left to extemporaneously combine different formulated products, which might even be incompatible with one another.

From a therapeutic point of view, it is therefore limiting for a patient not to be able to take the same drug in different conditions, such as at home, at work, while travelling and in an emergency. In the different situations indicated, a patient might be obliged to use different preparations containing different active agents.

The most important of the formulation problems encountered in the development of inhalation products concerns chemical stability in relation to atmospheric agents, which cause rapid degradation of the inhalation preparation and, consequently, decrease the shelf life of the product containing this preparation.

The stability of an inhalation product is particularly important, since it must be administered to the deep lung while maintaining its physical features for quantitative penetration of particles or droplets to the deepest regions thereof. Added to this is the fact that the number of excipients currently approved for inhalation administration and therefore acceptable in terms of toxicity for the pulmonary tissue is very limited.

The literature reports examples of dry inhalation powders with high dispersibility in air due to their low density. These powders are usually formulated with a high content of phospholipids, in particular dipalmitoylphosphatidylcholine (DPPC).

A powder of this kind is described in the patent application US2005/0074498 A1, relating to low density particles, with an internally hollow morphology, obtained by spray-drying with the use of surfactants constituted by phospholipids in combination with a blowing agent). The hollow structure is described as resulting from the precise combination of the blowing agent and of the surfactant phospholipid. The document does not describe examples of similar morphology obtained without phospholipids. The use of phospholipids as surfactants determines the principal features of the product obtained and above all its sensitivity and stability in relation to atmospheric agents, which would be particularly influenced in this case by moisture. Moreover, the patent literature (US 2001/0036481 A1) indicates values of the phospholipid transition temperature (Tg) with humidity of 41° C. for DPPC, 55° C. for di stearoylphosphatidylcholine (DSPC) and 63° C. for dipalmitoylphosphatidylethanolamine (DPPE), the three phospholipids most compatible with pulmonary administration.

The transition temperature is defined as the temperature required to cause a change in the physical state of the lipids, from the ordered gel phase in which the hydrocarbon chains are lying flat and closely packed, to the disordered liquid-crystalline phase in which the hydrocarbon chains are randomly oriented and fluid.

These Tg values are all much lower than the characteristic Tg value of amorphous lactose.

It is known that the closer the Tg is to the temperature of the environment in which the preparation is stored, the easier the transition will be. It is also known that in a system in which the main excipient is fluid and loosely packed, the molecular mobility of the components is very high, and consequently has a propensity to cause different chemical reactions and degradation of the active agents.

Therefore, the solution of producing porous particles for inhalation administration with phospholipids does not appear to be supported by reasonable scientific evaluation in relation to the long term stability of the product.

The aforesaid patent application, besides application as inhalation powder, also describes application of these particles in an inhaler device with a propellant gas. This administration would be impossible with a conventional nebulizer by dispersing the particles in water or aqueous solution, given the incompatibility of the materials with water, above all due to their tendency to float on the surface of the liquid or to dissolve slowly therein.

The concept of "high porosity" or "low density" has been used in a substantially equivalent manner in the cited patent applications.

In particular, the term "density" has been used not to refer to the absolute density of the particles, since this, measured with a helium pycnometer, would identify the density of the solid materials forming the powder and the particles according to the equation:

$$\rho = P/V (g/cc)$$

but rather to refer to the apparent density (in some documents by others described as "envelope density") of the particle, considering its overall volume.

Given the technical difficulty of measuring this overall volume for each single particle, the cited patent applications have referred to volume (and subsequently to density) parameters of the powder as bulk volume and tapped volume.

The patent application WO 03/0350030 A1 describes the preparation of a kit for inhalation administration that considers the preparation of a solid dry form containing a drug prepared by freeze-drying a solution. The process, also described through examples, presents great difficulties in relation to industrial production and, above all, provides no guarantees of substantial improvement of the stability of the active agent over time. In fact, after freeze-drying the drug added to the formulation is dispersed in an excipient network characterized by high porosity that cannot be modulated or modified through the process. Although it is useful from the point of view of rapid dissolution of the solid form, this porosity increases exposure of the drug to atmospheric agents and compromises its stability. In the specific case, no data are provided on the porosity of the freeze-dried products obtained in the examples, but literature data obtained through indirect measurements place the apparent density (corresponding to the bulk density of a powder) of formulated freeze-dried tablets containing sugars and surfactants between 0.05 and 0.2 g/cc.

The patent application CA2536319 describes a pharmaceutical composition obtained by spray drying, with a moisture content below 1%. According to what is indicated, this very low moisture content is necessary to ensure the stability of the composition, as a water content of over 1% in the formulation would cause degradation of the pharmacologically active substances, resulting in a loss of efficacy of the composition. To reduce the level of moisture the composition is constituted by a large amount of mannitol, which however compromises the physical features of the powder considerably, increasing the particle size and decreasing the dose of powder delivered from the mouthpiece of the inhalation device used.

The problem of producing inhalation powders with high dispersibility has been solved through the engineering of particles that contain the drug as dispersed as possible.

Briefly, the technique used is that of producing essentially fine particles (geometric mean diameter greater than 4.0 μm) consisting of small amounts of active agent dispersed at molecular level inside an appropriate matrix of excipients capable of guaranteeing, through the spray-drying preparation technique, the formation of a low density coarse particle.

This formulation approach requires the use of high percentages of excipients in the formulation, but enables small amounts of active agent to be contained in the composition.

For this reason, although these compositions solve the problem of aerodynamic performance, they fail to solve significant questions in terms of chemical stability.

The production of an inhalation powder in which the content % of active agent is high using a spray-drying technique must instead be considered advantageous in terms of chemical stability. Considering the common active agents of respiratory therapy, in the majority of cases this content % of active agent would be too high to allow the production of an inhalation powder form, given the limited amount of powder that constitutes an individual dose of product.

In fact, this amount of powder is too small to be dosed reproducibly by any industrial device for producing individual doses of inhalation powders.

Therefore, the production of an inhalation powder that is stable both from a chemical and physical point of view must necessarily reconcile the need for stability of the active agents used with the need to ensure adequate aerosol performance in terms of deposition in the deep lung.

From the point of view of chemical stability, an ideal approach is represented by the production of dry powders containing large amounts of active agent in combination with a sugar capable of decreasing molecular mobility in the particles of powder and a hydrophobic excipient capable of limiting interaction with the external environment and absorption of water by the powder.

From the point of view of aerosol performance, the same powder must be characterized by an adequate particle diameter for inhalation administration and by a composition capable of facilitating particle disaggregation at the time of inhalation.

At the same time, convergence of physical composition features of the powder must coincide with the ability to divide the powder evenly using devices for the industrial preparation of products in the form of inhalation powder in individual doses or of multidose inhalers capable of drawing a relatively large dose from a storage chamber contained therein.

Normally, in order to reproducibly deliver inhalation powders in an individual dose, carriers and inert fillers are used to enable rapid and efficient dilution of the active agent so that it can be easily metered in inhalers.

Lactose has been used as carrier in powder inhalation formulations (dry powder inhalers—DPI) since it was introduced in 1948 in the Aerohaler inhaler by Abbott.

In fact, lactose represents the only approved carrier for powder inhalation formulations and is used to produce homogeneous formulations in combination with micronized active agents facilitating division accuracy even the case of extremely small doses.

Inhalation formulations in powder form are generally produced as mixtures of coarse carrier particles combined with micronized particles of active agents generally with an aerodynamic diameter from 1-5 um.

Carrier particles are used to increase the flow of the particles of drug, thereby improving division accuracy and reducing variability of the dose observed in formulations containing only the active agent. With this formulation approach, it is possible to increase the size of the dose of powder to be handled, which otherwise would not exceed 1 mg total of active agent, facilitating handling and division of the bulk powders during production operations.

With the use of carrier particles, the particles of drug are emitted from the inhaler (single or multi-dose) more readily and therefore also the delivery efficiency of the powder is increased. The presence of a coarse carrier such as lactose also provides the patient with feedback during the inhalation phase, since it deposits on the taste buds and produces a blandly sweet sensation, confirming that the dose of drug has been taken correctly. Consequently, the lactose carrier represents an important component of the formulation and any changes to it in chemical and physical terms have the potential to alter the lung deposition profile of the drug. Therefore, the design of the carrier particles is important in the development of inhalation powder formulations.

During inhalation, the particles of drug adhering to the surface of the carrier particles detach as a result of the energy of the inhaled air flow that overcomes the adhesion forces between drug and carrier. The coarse particles of the carrier impact in the upper airways while the smaller particles of drug move through the lower airways and are deposited in the deep lung.

Insufficient detachment of the drug particles from those of the carrier due to strong interparticle energies must be considered the main cause of inefficient lung deposition of many powder inhalation products. Therefore, an effective inhalation formulation should be produced identifying the correct balance between adhesive and cohesive interparticle forces so as to guarantee sufficient adhesion between micronized drug and coarse lactose carrier to provide a stable formulation (with homogeneous mixtures and without segregation of powders and suitable uniformity of content) as well as guaranteeing efficacious detachment of the drug from the carrier during inhalation.

Consequently, the efficiency of a powder formulation depends greatly on the properties of the carrier and its selection is a key element for the general performance of the inhalation product. The range of materials that can be proposed for use as carrier in inhalation pharmaceutical products is extremely limited for toxicological reasons. Lactose and other sugars have been studied and used and consequently certain modifications of these materials can guarantee further formulation optimizations.

Various and controversial reports have been published regarding the most suitable sizes for a carrier for inhalation use. Some studies report improvements in the amounts of respirable drug delivered by a powder inhaler obtained through reducing the sizes of the carrier particles. It has been proposed that certain small agglomerates are more sensitive to turbulent motion in the inhaled air flow, causing more efficient deagglomeration. However, the use of a carrier that is too small causes a worsening in the flow properties of the powder, which is also one of the main reasons for incorporating a coarse carrier in the formulation. On the other hand, it has been reported that carrier particles that are too large normally exhibit larger surface discontinuities, than fine crystals. This can have the advantage of offering protection to the particles of active agent, preventing detachment during the mixing step. Therefore, a large particle size of the carrier is not necessarily a negative element from the point of view of drug deposition after inhalation. Thus, formulations with coarse carriers generally exhibit a better dispersion of the drug than similar formulations obtained with carrier particles of small size. This is due to weaker interparticle forces in the case of particles of larger sizes.

Even if the influence of the shape of the carrier particles on the dispersibility of the drug of a powder inhalation formulation is not well defined, it is known that the attractive forces between drug and carrier particles can depend on the morphology, in fact the most commonly used particles for powder inhalation formulations have irregular morphology.

In the light of all of the aforesaid considerations, it would be advantageous to be able to produce a pharmaceutical composition for inhalation use in the form of dry powder that is stable and easy to administer with common dispensers for inhalation powders, while remaining easy to produce. It would also be advantageous to obtain a solid composition in the form of dry powder, which can be used as diluent of inhalation powders in order to enable correct mixing of powders containing different active agents also in small amounts and at the same time maintains high stability of the formulation, preventing degradation of the active agents.

However, the problem of providing an inhalation formulation of drugs that is stable and administrable with common dispensers of inhalation powders, with features of high deliverability and respirability, and which can be produced with a commercially viable process, currently remains unsolved or unsatisfactorily solved.

Therefore, a first aspect of the present invention is to provide a pharmaceutical composition for inhalation use in powder form, comprising:

a) a first powder comprising at least a powder ($a_1$) comprising an active agent or a pharmaceutically acceptable salt thereof, in an amount greater than 1% by weight of said powder, leucine in an amount from 5 to 70% by weight of said powder, a sugar in an amount from 20 to 90% by weight of said powder;

b) a second powder comprising a mixture of a first lactose which has an X50 from 35 to 75 μm, with a second lactose which has an X50 from 1.5 to 10 μm, the content of said first and second lactose in said mixture being respectively from 85% to 96% and from 4% to 15%, wherein the ratio by weight between the first and the second powder included in the pharmaceutical composition is from 1/5 to 1/100.

The composition also has a fine particle fraction (FPF) greater than 60% and a delivered fraction (DF) greater than 80%.

A further aspect of the invention is represented by a Kit for administration of a drug as inhalation powder, comprising a metered amount of the composition according to the present invention and an inhalation device.

In a further embodiment of the pharmaceutical composition according to the present invention, the third powder ($a_2$) comprises a powder (hereinafter also defined as bulking agent) comprising leucine in an amount from 5 to 70% by weight of said second powder, a sugar in an amount from 20 to 90% by weight of said second powder.

With a pharmaceutical composition as described in this second embodiment, it is possible to obtain a pharmacologically active composition that can comprise an active agent that must be dosed in very small amounts both maintaining the ratio between first and second powder of the composition unchanged and guaranteeing high respirability.

In a further embodiment of the pharmaceutical composition according to the present invention, the first powder comprises a fourth powder ($a_3$) comprising an active agent, in an amount greater than 1% by weight of said third powder, leucine in an amount from 5 to 70% by weight of said third powder, a sugar in an amount from 20 to 90% by weight of said third powder.

With a pharmaceutical composition as described in this third embodiment, it is possible to obtain a pharmacologically active composition that can comprise the combination of two or more different active agents capable of acting synergically, or simply acting simultaneously in the site of application, so as to reduce the number of administrations.

According to the present invention, the term "active agent" is intended as any substance with a desired biological therapeutic efficacy.

Examples of active agents that can be administered by inhalation comprise: β2 agonists; steroids such as glucocorticosteroids or corticosteroids (preferably anti-inflammatory agents); anti-cholinergic agents; leukotriene antagonists; inhibitors of leukotriene synthesis; mucolytics; antibiotics, pain relievers in general such as analgesic and anti-inflammatory agents (including steroid and non-steroid anti-inflammatory agents); cardiovascular agents such as glucosides; respiratory agents; anti-asthma agents; short and long acting bronchodilator inhalers; anti-cancer agents; alkaloids (i.e. rye ergot alkaloids) or triptans such as sumatriptan or rizatriptan that can be used to treat migraine; agents (i.e. sulfonylurea) used to treat diabetes and related dysfunctions; sleep inducing drugs such as sedative and hypnotic agents; psychic energizers; appetite inhibitors; anti-arthritis agents; anti-malaria agents; anti-epileptic agents; anti-thrombotic agents; anti-hypertensive agents; anti-arrhythmic agents; anti-oxidant agents; anti-psychotic agents; anxyolitics; anti-convulsant agents; anti-emetic agents; anti-infective agents; anti-histamines; anti-fungus and anti-viral agents; drugs to treat neurological dysfunctions such as Parkinson's disease (dopamine antagonists); drugs to treat alcoholism and other forms of addiction; drugs such as vasodilators to treat erectile dysfunction; muscle relaxants; muscle contractors; opioids; stimulating agents; tranquilizers; antibiotics such as macrolides; aminoglycosides; fluoroquinolones and β-lactames; vaccines; cytokines; growth factors; hormones including birth-control drugs; sympathomimetic agents; diuretics; lipid regulating agents; anti-androgen agents; anti-parasitics; blood thinners; neoplastic agents; anti-neoplastic agents; hypoglycemic agents; nutritional agents and supplements; growth supplements; anti-enteric agents; vaccines; antibodies; diagnostic and contrast agents; or mixtures of the above substances (e.g. combinations for the treatment of asthma containing steroids and β-agonists); heparin and its derivatives such as heparins with molecular weight from 15 to 30 Kda and semi-synthetic heparin derivatives; substances with antioxidant action such as N-acetylcysteine, Carnosine, Melatonin, Resveratrol, Ascorbic Acid, Alpha-tocopherol, Folic Acid, Trans-caffeic Acid, Hesperidin, Epi-gallocatechin-gallate, Delphinidin, Rosmarinic Acid, Myricetin, 5-methyltetrahydrofolic acid, 5-formyltetrahydrofolate acid, 5-formyl tetrahydrofolic acid, Astaxanthin, Lycopene, Curcumin, Pinostilbene, Pterostilbene and Isorhapontigenin.

The aforesaid active agents belong to one or more structural classes, including, but not limited to, small molecules (preferably small insoluble molecules), peptides, polypeptides, proteins, polysaccharides, steroids, nucleotides, oligonucleotides, polynucleotides, fats, electrolytes and the like.

Specific examples include the β2-agonists salbutamol, salmeterol (i.e. salmeterol xinafoate), formoterol and formoterol fumarate, fenoterol, indacaterol, olodaterol, vilanterol, levalbuterol and carmoterol, steroids such as beclomethasone dipropionate, budesonide and fluticasone (e.g. fluticasone proprionate or fluticasone furoate), ciclesonide, mometasone furoate, anti-cholinergics such as glycopyrronium bromide, aclidinium bromide, umeclidinium, ipratropium bromide, oxitropium, tiotropium bromide;

With regard to peptides and proteins, the present invention also comprises synthetic, recombinant, native, glycosylated and non-glycosylated peptides and proteins and biologically active fragments and analogs.

Active agents for which an immediate release into the bloodstream is particularly advantageous to obtain a rapid pharmacological effect include those to be used to treat migraine, nausea, insomnia, allergic reactions (including anaphylactic reactions), neurological and psychiatric disorders (in particular panic attacks and other psychoses or neuroses as well as Parkinson's disease), among these active agents, levodopa and monoamine oxidase inhibitors including safinamide, erectile dysfunction, diabetes and related diseases, heart diseases, anti-convulsive agents, bronchodilators and active agents to treat pain and inflammation. According to the present invention, vaccines constituted by antibodies, cells, corpuscles and cellular portions can also be administered.

Other examples of active substances are steroids and their salts, such as budesonide, testosterone, progesterone, flunisolide, triamcinolone, beclomethasone, betamethasone, dexamethasone, fluticasone, methylprednisolone, prednisone, hydrocortisone and the like; peptides such as cyclosporine and other water-insoluble peptides; retinoids such as cis-retinoic acid, 13-trans-retinoic acid and other derivatives of vitamin A and of beta-carotene; vitamins D, E and K and their precursors and water-insoluble derivatives; prostaglandins, leukotrienes and their activators and inhibitors including prostacyclin, prostaglandins E1 and E2, tetrahydrocannabinol, pulmonary surfactant lipids; lipid-soluble anti-oxidants; hydrophobic antibiotics and chemotherapic drugs such as amphotericin B, adriamycin and the like.

A further example of active substance is pirfenidone, employed in the treatment of idiopathic pulmonary fibrosis.

In particular, according to the present invention the active agent is a hydrolyzable active agent, i.e. a substance capable of undergoing degradation processes as a function of the amount of water present in the formulation.

According to the present invention, the term "sugar" is intended as monosaccharides with 5 or more carbon atoms, disaccharides, oligosaccharides or polysaccharides and also polyols with 5 or more carbon atoms (often also defined as sugar-alcohol)

Examples of sugars that can be administered by inhalation comprise: lactose, trehalose, sucrose, maltose, melibiose, cellobiose, mannitol, dextrins, maltodextrins, sorbitol, galactitol, iditol, volemitol, fucitol, inositol, maltitol, lactitol, isomalt, maltotriose, maltotetraose, polyglycitol.

The amount of sugar present in the powders ($a_1$, $a_2$, $a_3$) contained in the first powder of the pharmaceutical composition of the present description is from 20 to 90% by weight of each powder, preferably in an amount from 20 to 80% by weight of each powder, even more preferably in an amount from 40 to 80% by weight of each powder.

According to the present invention the powders ($a_1$, $a_2$, $a_3$) contained in the first powder of the pharmaceutical composition of the present description include a hydrophobic substance to reduce moisture sensitivity. This hydrophobic substance is leucine, which also facilitates particle disaggregation. Leucine is present in an amount from 5 to 70% by weight of each powder, preferably in an amount from 15 to 70% by weight of each powder, even more preferably in an amount from 18 to 55% by weight of each powder.

According to the present invention, the powders ($a_1$, $a_2$, $a_3$) contained in the first powder of the pharmaceutical composition of the present description include a surfactant in an amount from 0.2 to 2.0% by weight of each powder, preferably in an amount from 0.4 to 0.8% by weight of each powder.

The surfactant of the pharmaceutical composition according to the invention can be selected from the various classes of surfactants for pharmaceutical use.

Surfactants suitable to be used in the present invention are all those substances characterized by medium or low molecular weight containing a hydrophobic moiety, generally readily soluble in an organic solvent but weakly soluble or totally insoluble in water, and a hydrophilic (or polar) moiety, weakly soluble or completely insoluble in an organic solvent but readily soluble in water. Surfactants are classified according to their polar moiety. Therefore, surfactants with a negatively charged polar moiety are called anionic surfactants, while cationic surfactants contain a positively charged polar moiety. Uncharged surfactants are generally called non ionic, while surfactants with both a positive and negative charge are called zwitterionic. Examples of anionic surfactants are represented by the salts of fatty acids (better known as soaps), sulfates, sulfate ethers and phosphate esters. Cationic surfactants are frequently based on polar groups containing amino groups. The most common non ionic surfactants are based on polar groups containing oligo-(ethylene-oxide) groups. Zwitterionic surfactants are generally characterized by a polar group constituted by a quaternary amine and a sulfuric or carboxylic group.

Specific examples of this application are represented by the following surfactants: benzalkonium chloride, cetrimide, docusate sodium, glyceryl monooleate, sorbitan esters, sodium lauryl sulphate, polysorbates, phospholipids, bile salts.

Non ionic surfactants, such as polysorbates and polyoxyethylene and polyoxypropylene block copolymers, known as "Poloxamers", are preferred. Polysorbates are described in the CTFA International Cosmetic Ingredient Dictionary as mixtures of sorbitol and sorbitol anhydride fatty acid esters condensed with ethylene oxide. Particularly preferred are non ionic surfactants of the series known as "Tween", in particular the surfactant known as "Tween 80", a polyoxyethylene sorbitan monooleate available on the market.

The presence of a surfactant, and preferably of Tween 80, is necessary to reduce the electrostatic charges found in formulations without it, flow of the powder and maintenance of a homogeneous solid state without initial crystallization.

According to the present invention, the term "inhalable" is intended as a powder suitable for pulmonary administration. An inhalable powder can be dispersed and inhaled by means of an appropriate inhaler, so that the particle can enter the lungs and alveoli to provide the pharmacological features of the active agent of which it is formed. A particle with aerodynamic diameter of less than 5.0 µm is normally considered inhalable.

The term "amorphous" according to the present invention is intended as a powder that contains less than 70% of crystalline fraction, more preferably less than 55%. The pharmaceutical composition described in this text has a ratio between the amount of powder in amorphous form that constitutes the composition expressed by weight and the amount of sugar present in the composition expressed by weight ranging from 0.8 to 2.0. This ratio indicates that the sugar present in the powder is a substantially amorphous sugar, which therefore has a crystalline fraction of less than 50%. This enables the sugar to coordinate the water present in the composition, preventing it from being available to hydrolyze the active agent, thereby making it ineffective.

The term "fine particle fraction (FPF)" is intended as the fraction of powder, with respect to the total delivered by an inhaler, which has an aerodynamic diameter (dae) of less than 5.0 µm. The term "delivered fraction (DF)" is intended as the fraction of active agent delivered, with respect to the total loaded. The characterization test that is performed to evaluate these properties of the powder is the Multi Stage Liquid Impinger (MSLI) test, as described in the European Pharmacopoeia current ed. The conditions for performing this test consist in subjecting the powder to an inhalation through the inhaler such as to generate a flow of 60±2 liters/min. This flow in the case of the Model RS01 Inhaler (Plastiape, Osnago, IT) is obtained by generating a pressure drop of 2 KPa in the system.

The preferred production process of the powder or powders constituting the first powder according to the invention is spray drying starting from a solution of leucine, of a sugar and a surfactant in which the drug, if present, is dissolved or dispersed as suspension or emulsion.

The preferred particle size for this first powder provides that at least 50% of the size distribution (X50) is below 5 µm, preferably below 3 µm, more preferably below 2.0 µm, also to increase the surface area optimizing deep lung deposition.

According to the present invention, the powder or powders that constitute the first powder of the pharmaceutical composition according to the present description is a substantially dry powder, i.e. a powder with a moisture content of less than 10%, preferably less than 5%, more preferably below 3%. This dry powder preferably has no water capable of hydrolyzing the active agent making it inactive. The amount of moisture present in the composition is controlled by the presence of leucine, which limits the content due to its hydrophic features, both in the step to produce the powder and in the subsequent handling steps, and of sugar, which traps the water in a structure that becomes increasingly rigid over time, preventing the water from hydrolyzing the active agent.

According to the present invention the second powder included in the pharmaceutical composition for inhalation use comprises a mixture of two types of lactose with different particle size. With this powder it is possible to obtain a composition that can be easily divided in the means used for administration, such as the capsules used in inhalation systems, and at the same time obtain a composition with high respirability so that the active agent or agents used can be deposited in deep lung regions and perform their pharmacological action.

According to what is described above, a composition comprising a second lactose powder that is too fine or too coarse is not an ideal solution for obtaining the respirability results desired. Therefore, the possibility of adding an amount of fine particles of lactose to formulations of inhalation powders already containing coarse lactose powders in order to improve the inhalation efficiency of drugs was evaluated.

Studies conducted confirmed that the presence of fine lactose well associated with coarser lactose is capable of performing a key role in the drug dispersion process. In a preferred embodiment, the addition of around 10% of fine lactose mixed with coarse lactose showed that the fine component helps the particles including the active agent to detach from the coarse particles. It was also reported that the concentration of fine lactose added must be carefully controlled since the desired dispersibility of the drug can be reached without substantially influencing the flow properties of the drug. On the contrary, the presence of an excess of fine lactose tends to inhibit flow of the powder since this can enter the voids between the larger particles and promote compacting and consequent thickening of the powder. It was also reported that the presence of an excess of fine lactose causes a decrease of the respirable fraction of an inhalation powder.

According to the present invention, the mixture comprises a lactose with larger particle size, i.e. with an X50 (at least 50% of the particles) from 35 to 75 μm present in an amount greater than a second lactose with smaller particle size, i.e. with an X50 from 1.5 to 10 μm. In particular, the lactose with larger particle size is present in the mixture in a percentage by weight of the mixture from 85 to 96%, while the lactose with smaller particle size is present in the mixture in a percentage by weight of the mixture from 4 to 15%. Preferably, the lactose with larger particle size is present in the mixture in a percentage by weight of the mixture from 91 to 95%, while the lactose with smaller particle size is present in the mixture in a percentage by weight of the mixture from 5 to 9%.

In order to obtain a composition having properties of high respirability, the particles of the first powder constituting the pharmaceutical composition must be in an amount that ensures easy detachment thereof from the lactose particles that form the second powder. Therefore, the ratio between the first and the second powder comprising the mixture of lactoses must be from 1/100 to 1/5. This ratio provides the composition with high respirability, guaranteeing good pharmacological response of the active agent.

For some active agents, whose doses in the pharmaceutical composition to be administered are very low and consequently insufficient to ensure an adequate ratio between first and second powder, the first powder also comprises an inert powder from a pharmacological point of view capable of increasing the amount of first powder with respect to the second powder so as to guarantee an aerodynamic performance that allows the active agent to reach the site of action.

The process for preparing the pharmaceutical composition according to the invention substantially comprises the operations of:

a) providing a first powder comprising at least a powder obtained by spray drying comprising an active agent in an amount greater than 1% by weight of the powder, leucine in an amount ranging from 5 to 70% by weight of the powder, a sugar substantially amorphous after obtaining the powder by spray drying in an amount ranging from 20 to 90% by weight of the powder;

b) providing a second powder obtained by mixing a first lactose which has an X50 from 35 to 75 μm, with a second lactose which has an X50 from 1.5 to 10 μm, the content of the first and second lactose in the mixture being respectively from 85% to 96% and from 4% to 15%, c) mixing the powders.

In particular, the production process of the composition, in step a) of obtaining the powder or powders by spray drying, consists of a series of operations illustrated below:

For step a):

preparing a first phase (A) in which an active agent is present in an appropriate liquid medium;

preparing a second phase (B) in which the leucine, the sugar and surfactants are dissolved or dispersed in an aqueous medium;

mixing said phases (A) and (B) to obtain a third phase (C) in which the liquid medium is homogeneous;

drying said phase (C) in controlled conditions to obtain a dry powder with particles having a size distribution with median diameter of less than 10.0 μm;

collecting said dry powder.

Phase (A) can be either a suspension of the active agent in an aqueous or non aqueous medium, or a solution of the active agent in an appropriate solvent.

Preparation of a solution is preferable, and the organic solvent is selected from those soluble in water. In this case, phase (C) is also a solution of all the components of the desired composition.

Instead, when phase (A) is a suspension of the hydrophobic active agent in an aqueous medium, phase (C) is also a suspension in an aqueous medium, which will contain the dissolved soluble components such as the excipients and surfactants.

The drying operation consists of eliminating the liquid medium, solvent or dispersant, from phase (C), to obtain a dry powder with the desired dimensional features. This drying is preferably obtained by spray-drying. The features of the nozzle and the process parameters are selected so that the liquid medium is evaporated from the solution or suspension (C) and a powder with the desired particle size is formed.

The production process of the composition, in step b) of obtaining the mixture of lactose, consists of physical mixing of lactoses with different particles sizes obtained according to normal mixing techniques. In a preferred embodiment of the invention, the lactoses used are Respitose® SV003 (DFE Pharma, Goch, D) and Lacto-Sphere® MM3 (Microsphere SA, Ponte Cremenaga, Lugano CH).

Step c) of the process for preparing the pharmaceutical composition instead consists of physical mixing of the powders obtained by spray draying and of the lactose mixture using the most common mixing techniques, i.e. rotating mixers such as Turbula, V-mixer, cylinder, double cone, cube mixers or stationary mixers used only for mixing, such as planetary, nautamix, sigma, ribbon mixers or mixer-granulators, such as Diosna. Besides these mixers, the powders could also be mixed with devices normally used to mix liquids, such as Ultra Turrax or Silverson and, ultimately, also inside fluid bed granulation apparatus.

As already indicated above, the first powder constituting the pharmaceutical composition according to the present invention can comprise a powder, called bulking agent (BA), comprising leucine in an amount from 5 to 70% by weight of the powder; a sugar in an amount from 20 to 90% by weight of the powder, in which the composition has a fine particle fraction (FPF) greater than 60% and a percentage of the dose delivered from the mouthpiece (DF) greater than 80%.

This composition can be used to increase the amount of the first powder with respect to the second powder comprising the mixture of lactose guaranteeing the correct ratio between the two powders, maintaining properties of high respirability of the composition according to the invention.

The production process of the bulking agent is substantially similar to the process for preparing the powder containing the active agent (step a), in particular, this process consists of the following operations:

preparing a first phase (A) in which the leucine, the sugar and surfactants are dissolved or dispersed in an aqueous medium;

drying said phase (A) in controlled conditions to obtain a dry powder with particles with a size distribution having a median diameter of less than 10.0 μm;

collecting said dry powder.

EXAMPLES

The methods for preparing the powders that constitute the pharmaceutical composition and for preparing the solid composition for use as diluent (hereinafter bulking agent) of the present invention will now be described.

Preparation of the Individual Powders.

The powders containing the active agents and the bulking agent were obtained by spray drying, a drying technique used to obtain powders with uniform and amorphous particles from solutions of active agents and excipients in appropriate solvent or mixture of solvents.

For the formulations described the solvents used are water and ethyl alcohol in a fixed ratio of 70/30. The concentration of dissolved solids is 1% w/v for formulations containing the active agent and 2% w/v for the bulking agent.

In the case of the powder containing as active agent Formoterol Fumarate, tiotropium bromide and bulking agent, all the components of the powder were dissolved in water and the solution thus obtained was added to the portion of ethyl alcohol slowly at 25° C., taking care not to cause precipitation of some of the components.

For the formulation containing Budesonide as active agent, the active agent was dissolved separately in the alcohol portion to which the aqueous solution of the excipients was added to obtain a single water-alcohol solution.

The water-alcohol solution thus obtained was processed by means of a Buchi Mod. B290 spray dryer, using an open cycle with the following parameters:

nozzle diameter 0.7 mm
atomization gas nitrogen
atomization pressure 4 bar
drying gas air
aspiration 100% (35 m3/h)
inlet temperature 170° C.
feed speed 8% (2.4 ml/min)

Powder collection system: cyclone separator with glass collection vessel

Outlet filter: polyester sleeve.

At the end of the drying process the powder collection step was performed in controlled temperature and humidity conditions: temperature<25° C., relative humidity<35%.

The powders were packaged immediately after production in borosilicate glass vials inserted in a double aluminum foil bag heat-sealed under partial vacuum (30%).

Storage Conditions for Accelerated Stability Study.

The powders produced by spray drying, divided and packaged in borosilicate glass vials sealed inside in a double aluminum foil bag heat-sealed under partial vacuum (30%) were stored for an accelerated stability study in an oven at a temperature of 40° C. and relative humidity of 13%.

At each time interval established by the study, the samples corresponding to the stability point were taken, left to cool until reaching room temperature, opened in controlled conditions in a glove box (temperature<20° C., RH<35%) and analyzed as established in the protocol.

Characterization of the Powder: Particle Size Analysis.

The powders obtained after spray drying were characterized in terms of dry particle size using a Sympatec Helos light scattering device that analyzes the particle size according to the Fraunhofer theory and equipped with RODOS disperser.

The instrument was suitably calibrated with reference material and prepared following the instructions provided in the instrument user manual.

After appropriate cleaning before analysis, an amount of powder for each batch produced was analyzed without any preliminary preparation of the sample.

The dispersion gas used was compressed air suitably cleansed of particles.

The test method specified therefore provides for compliance with the following measures in relation to the sample, to the powder disperser and to the light scattering analyzer.

Sample
size: about 100 mg
feed procedure: with a spatula
pre-treatment of the sample: none
RODOS Disperser
Model M ID-NR 230 V/Hz 24Va
Dispersion pressure: 3 bar
Light Scattering Analyzer
Model: Helos
Test method: Fraunhofer
Software version: Windox 4.0
Test lens: R1 (0.1-35 μm)
Minimum optical concentration: 1%
Activation threshold: minimum optical concentration detectable 1% for max 30 seconds of time and with at least 100 ms of exposure of the sample.

All the tests were conducted in controlled temperature and humidity environments, temperature<25° C. and relative humidity<50% RH.

Size analysis provides volume median diameter (VMD) values of the population of particles in the sample of powder.

Characterization of the Powder: Residual Moisture Content.

The residual moisture content in the powder obtained by spray drying was measured using the Karl Fischer coulometric system method.

The C20 Compact Karl Fischer Coulometer Mettler Toledo titrator was used for this purpose, which uses as reagent HYDRANAL®-Coulomat AG.

The sample powders were accurately weighed in an amount of around 15-20 mg and the weight was recorded in the parameters of the sample. Titration was started immediately after adding the sample to the reagent bath.

At the end of the test, the instrument indicates directly the percentage of water contained in the sample.

Characterization of the Powder: Determination of Titer and Related.

Three different HPLC (High Performance Liquid Chromatography) methods were used to determine the content of active agents in samples from MSLI tests and in the formulations, as well as of their related substances, as set down below:

Method 1: Determination of formoterol and budesonide in MSLI samples
  Determination of the titer of formoterol and budesonide
  Determination of the degradation products of formoterol and budesonide
Method 2: Determination of tiotropium in MSLI samples (also in the presence of formoterol and/or budesonide)
Method 3: Determination of the tiotropium titer (also in the presence of formoterol and/or budesonide)
  Determination of the degradation products (also in the presence of formoterol and/or budesonide)

Method 1

The test method used to determine the content in MSLI samples, titer and degradation products for formulations containing Formoterol/Budesonide, is characterized by the following parameters:

Solvent: 50/50 methanol/phosphate buffer pH 2.7 25 mM
Mobile phase: acetonitrile/phosphate buffer pH 2.9 2.82 mM
gradient elution

| Time (min) | % ACN | % buffer pH 2.9 | Flow (ml/min) |
|---|---|---|---|
| 0 | 22 | 78 | 0.5 |
| 2.5 | 22 | 78 | 0.5 |
| 3.0 | 41 | 59 | 0.7 |
| 8.0 | 41 | 59 | 0.7 |
| 10.0 | 70 | 30 | 0.7 |
| 12.0 | 22 | 78 | 0.6 |
| 15.0 | 22 | 78 | 0.6 |

Injection volume: 20 μL
Analysis column: Agilent Poroshell 120 EC-C18, 100 mm×3.0 mm, 2.7 μm
Column temperature: 30° C.
Wavelength: 220 nm (Formoterol Fumarate) and 240 nm (Budesonide)
Retention time: 2.4 min (Formoterol Fumarate) and 8.0 min (Budesonide)
An HPLC Agilent model 1200 with diode array type detector, model G1315C was used for the test.

The samples for analysis were obtained by dissolving in the solvent an amount of powder such as to obtain a concentration of 160 μg/ml for the Budesonide and 4.5 μg/ml for the Formoterol Fumarate, as for the reference solution.

The reference solution was injected three consecutive times before the sample to determine the precision of the system expressed as relative standard deviation percentage (RSD %), which must be less than 2%.

The active agent content is obtained by calculating the ratio of the areas with respect to the reference solution at known concentration. The degradation of the product is calculated as ratio between the sum of the areas of all the analysis peaks corresponding to the degradation products and the active agent taken as reference. All the analysis peaks whose chromatogram area was greater than 0.1% of the area of the active agent are counted in the sum of the degradation products.

Method 2

The test method used to determine the Tiotropium content in MSLI samples, alone or in combination with Formoterol and/or Budesonide, is characterized by the following parameters:

Solvent: 40/60 methanol/phosphate buffer pH 2.7 25 mM
Mobile phase: acetonitrile/phosphate buffer pH 2.9 2.82 mM
gradient elution

| Time (min) | % ACN | % buffer pH 2.9 | Flow (ml/min) |
|---|---|---|---|
| 0 | 22 | 78 | 0.5 |
| 2.9 | 22 | 78 | 0.5 |
| 3.3 | 22 | 78 | 1.0 |
| 4.0 | 22 | 78 | 1.0 |
| 4.1 | 41 | 59 | 0.7 |
| 9.0 | 41 | 59 | 0.7 |
| 11.0 | 80 | 20 | 0.6 |
| 13.0 | 22 | 78 | 0.6 |
| 16.0 | 22 | 78 | 0.6 |

Injection volume: 20 μL
Analysis column: Agilent Poroshell 120 EC-C18, 100 mm×3.0 mm, 2.7 μm
Column temperature: 30° C.
Wavelength: 220 nm (Formoterol Fumarate) and 240 nm (Tiotropium-Budesonide)
Retention time: 2.3 min Formoterol Fumarate; 3.5 min Tiotropium; 9.0 min Budesonide.
An HPLC Agilent model 1200 with diode array type detector, model G1315C was used for the test.

The reference solution was injected three consecutive times before the sample to determine the precision of the system expressed as relative standard deviation percentage (RSD %), which must be less than 2%.

The active agent content is obtained by calculating the ratio of the areas with respect to the reference solution at known concentration.

Method 3

The test method used to determine the titer and degradation products for formulations containing Tiotropium is characterized by the following parameters:

Solvent: 40/60 methanol/phosphate buffer pH 2.7 25 mM
Mobile phase: acetonitrile/phosphate buffer pH 2.9 2.82 mM
gradient elution

| Time (min) | % ACN | % buffer pH 2.9 | Flow (ml/min) |
|---|---|---|---|
| 0 | 20 | 80 | 0.7 |
| 6 | 20 | 80 | 1.0 |
| 15 | 25.6 | 74.4 | 1.0 |
| 15.5 | 25.6 | 74.4 | 1.2 |
| 18 | 32 | 68 | 1.2 |
| 25 | 40 | 60 | 1.2 |
| 28 | 60 | 40 | 1.2 |
| 29 | 60 | 40 | 1.4 |
| 33 | 70 | 30 | 1.4 |
| 35 | 70 | 30 | 0.7 |
| 40 | 20 | 80 | 0.7 |
| 60 | 20 | 80 | 0.7 |

Injection volume: 20 μL
Analysis column: Agilent Poroshell 120 EC-C18, 150 mm×4.6 mm, 2.7 μm
Column temperature: 30° C.
Wavelength: 240 nm-Tiotropium; 315 imp.F Tiotropium.
Retention time: 9 min Tiotropium;
An HPLC Agilent model 1200 with diode array type detector, model G1315C was used for the test.

The samples for analysis were obtained by dissolving in the solvent an amount of powder such as to obtain a concentration of 6 µg/ml for Tiotropium Bromide, as for the reference solution.

The reference solution was injected three consecutive times before the sample to determine the precision of the system expressed as relative standard deviation percentage (RSD %), which must be less than 2%.

The content in active agents is obtained by calculating the ratio of the areas with respect to the reference solution at known concentration. The degradation of the product is calculated as ratio between the sum of the areas of all the analysis peaks corresponding to the degradation products and the active agent taken as reference. All the analysis peaks whose chromatogram area was greater than 0.1% of the area of the active agent are counted in the sum of the degradation products.

Characterization of the Powder: Differential Scanning Calorimetry.

Differential scanning calorimetry or DSC is a thermoanalytical technique used to determine chemical and physical phenomena with endothermic or exothermic effect in a sample, such as variations in phase, loss of water, chemical reactions.

In DSC the sample is heated with constant heating speed and the amount of heat required to raise its temperature is a function of its thermal capacity. Each endothermic or exothermic phenomenon causes a reversible or irreversible change in the thermal capacity of the material and can be detected as a variation of the baseline of the thermogram.

Formulations containing amorphous lactose show during heating a typical decrease in thermal capacity corresponding to the glass transition of the lactose from amorphous solid state to a metastable state that rapidly leads to its crystallization, characterized by an exothermic peak.

The temperature corresponding to these phenomena varies as a function of the composition of the sample and of the environmental conditions in which the sample is stored and prepared.

The samples were prepared in a controlled environment (temperature<20° C., relative humidity 35-30%). 40 uL aluminum standard crucibles for DSC were filled with a weighed amount of powder between 1 mg and 3 mg and sealed with specific lid.

Calorimetry testing of the samples in question was carried out by subjecting the samples to a heating ramp from 20 to 200° C. with a temperature increase of 10° C./min.

The test gives a thermogram in which the thermal events that accompany progressive heating of the sample are visible.

The glass transition (Tg) is identifiable with a decreasing step, at times followed by an increase in the baseline caused by relaxation enthalpy. During evaluation of the thermograms the onset temperature of the phenomenon (Tg onset) is calculated, regardless of the sample size. The glass transition temperature is a stability index of the powder as it is a prelude to crystallization, which takes place above 100° C. The exothermic crystallization peak can be integrated and the area subtended by the curve is an index of the amorphous fraction of the sample.

Preparation of the Mixtures.

The formulations used for the aerosol characterization tests with MSLI were produced by mixing powders containing the active agents and bulking agent with the mixture of lactoses. The powders were mixed using an Ultra Turrax T10 mixer for a mixing time of 5 minutes considered sufficient for the 3.5 g of powder of the batches produced. Uniformity of the content was controlled with titer analysis on 10 samples taken from different points of the bulk.

The powders were divided in sealed vials and stored inside a double aluminum foil bag heat sealed with partial vacuum (30%).

The operations of mixing and dividing in vials were carried out inside a glove box in controlled humidity and temperature conditions; max temperature 20° C. and environmental relative humidity<35%.

Characterization of the Powder: Respirability Test with MSLI.

The Multi Stage Liquid Impinger (MSLI) is a device that simulates in vitro pulmonary deposition of an inhalation formulation. A inhalation formulation, delivered by appropriate inhaler and conveyed into the device by aspiration, is deposited in the various stages connected in series of the impactor as a function of its aerodynamic features, such as particle size, density, shape. Each stage of the MSLI corresponds to an interval of aerodynamic particle sizes of the powder deposited therein and the aerodynamic size distribution of the powder is obtained using HPLC testing to determine the amount of active agent in each stage, making it possible to calculate the median aerodynamic diameter and the respirable fraction, considered according to the European Pharmacopoeia with aerodynamic diameter<5.0 μm.

For the respirability test, the powders of the formulations of the examples were divided into Size 3 HPMC capsules and loaded from RS01 powder inhaler—model 7 single-dose, code 239700001AB (Plastiape S.p.A.).

The device was assembled following the instructions for use and the indications of the European Pharmacopoeia.

For test purposes, it is necessary to deliver 10 powder capsules for each respirability test. The tests can be conducted at different pressure drops. In the case of the inhaler RS01, the pressure drop of 2 KPa corresponds to a flow of 60±2 l/min for 4 seconds and the pressure drop of 4 KPa records a flow of 96±2 l/min for 2.4 s. derived from a pressure drop of 2 Kpa in the system.

The following aerodynamic diameter cut-offs correspond to this flow value for each stage.

| Stage | Aerodynamic range diam. 2 KPa (60 ± 2 l/min) | Aerodynamic range diam. 4 KPa (96 ± 2 l/min) |
|---|---|---|
| 1 | >13 μm | >10.3 μm |
| 2 | 13.0-6.8 μm | 10.3-5.4 μm |
| 3 | 6.8-3.1 μm | 5.4-2.5 μm |
| 4 | 3.1-1.7 μm | 2.5-1.3 μm |
| 5 (filter): | <1.7 μm | <1.3 μm |

The respirable fraction (Fine Particle Fraction) comprises particles having a median aerodynamic diameter of less than 5 μm and is calculated using specific software (CITDAS Copley).

The aerodynamic parameters of an inhalation formulation subjected to MSLI analysis are expressed in terms of:

Delivered Fraction (DF): i.e. the percentage of the dose of active agent delivered from the mouthpiece of the inhaler Fine Particle Fraction (FPF): respirable fraction (aerodynamic diameter<5.0 μm) of active agent expressed as percentage of the amount delivered.

Quantitative determination of the active agent in each stage was performed by HPLC using the test method for titer and related.

Example 1

Example 1 was conducted producing formulations containing Formoterol Fumarate or Tiotropium Bromide, which are two active agents sensitive to the presence of free water in the formulation.

In the case of formoterol, formulations containing different amounts of leucine and lactose or mannitol were produced.

The example highlights the protective effect of lactose against formoterol, this protective effect is explained considering that lactose is capable of producing a scavenger effect against the free water present in the formulation.

To demonstrate this, formulations of 3 types were produced:

A powder containing exclusively formoterol and leucine
2 powders with different lactose contents together with formoterol and leucine
2 powders containing formoterol and leucine in which lactose was substituted by a different sugar: mannitol The formulations with lactose tend to acquire moisture over time, with consequent decrease of Tg, but degradation over time is limited. This limited degradation is presumably due to a scavenger effect produced by the lactose against the water, which is thus trapped in a rigid structure and prevented from reacting with the other components. Differently, the formulation without lactose which was already crystalline undergoes chemical degradation.

Of the two formulations containing lactose, the one with 50% is better, as it is more stable over time.

Formulations containing tiotropium, leucine and lactose at different concentrations of tiotropium were also produced to assess the minimum concentration of active agent in the formulation so as to obtain a stable powder.

Example 2

The example was conducted producing formulations containing as active agent Budesonide, defined as HLSA Bud, formulated with lactose and leucine (Table 3), formulations containing as active agent Formoterol Fumarate, defined as HLSA FF, formulated with lactose and leucine (Table 2).

The lactose powders used were Respitose® SV003 (DFE Pharma, Goch, D) e Lacto-Sphere® MM3 (Microsphere SA, Ponte Cremenaga, Lugano CH).

Identification of the optimal coarse/fine lactose ratio was based on the production of formulations with increasing amounts of LactoSphere MM3 in formulations containing HLSA FF, HLSA Bud and Respitose SV003 due to the aerodynamic characterization of each single formulation. The parameters evaluated through the MSLI test were the Fine Particle Fraction (FPF %) and the Delivered Fraction (DF %) in conditions with pressure drop of 4 KPa using the inhaler RS01 (Plastiape, Osnago, Lecco, I).

The results obtained show that a ratio of 91:9 Respitose SV003 (coarse lactose) and MM3 (fine lactose) guarantees high values of Delivered Dose (%) and high Fine Particle Fraction (%) respirability, at the same time ensuring that the mixture remains homogeneous over time.

TABLE 2

| Powder containing Formoterol Fumarate (HLSA FF 2.25%) | |
|---|---|
| Formoterol Fumarate | 2.25% |
| Leucine | 20.0% |
| Lactose | 77.25% |
| Tween 80 | 0.5% |

TABLE 1A

| Ex. | Formoterol (%) | Tiotropium (%) | Leucine (%) | Lactose (%) | Mannitol (%) | Tween 80 (%) | Water content (%) T0 | Water content (%) T28 days |
|---|---|---|---|---|---|---|---|---|
| 1 | 5.00 | | 95.00 | | | | 0.9 | 0.9 |
| 2 | 5.00 | | 70.00 | 25.00 | | | 1.4 | 1.8 |
| 3 | 5.00 | | 45.00 | 50.00 | | | 2.1 | 2.7 |
| 4 | 5.00 | | 70.00 | | 25.00 | | 0.9 | 0.9 |
| 5 | 5.00 | | 45.00 | | 50.00 | | 1.0 | 0.9 |
| 6 | | 0.06 | 50.00 | 49.44 | | 0.50 | 1.2 | 2.0 |
| 7 | | 3.00 | 50.00 | 46.50 | | 0.50 | 3.0 | 2.5 |
| 8 | | 6.00 | 50.00 | 43.50 | | 0.50 | 2.4 | 1.3 |

TABLE 1B

| Ex. | Tg (° C.) T0 | Tg (° C.) T28 days | P. size (VMD) T0 | P. size (VMD) T28 days | Degradation products (%) T0 | Degradation products (%) T28 days |
|---|---|---|---|---|---|---|
| 1 | Not detected | Not detected | 2.6 | 2.7 | 0.6 | 0.9 |
| 2 | 62.7 | 56.9 | 2.0 | 1.9 | 0.4 | 0.4 |
| 3 | 66.3 | 57.5 | 1.6 | 1.6 | 0.3 | 0.3 |
| 4 | Not detected | Not detected | 2.3 | 2.2 | 0.2 | 1.6 |
| 5 | Not detected | Not detected | 1.6 | 1.6 | 0.1 | 1.4 |
| 6 | 72.7 | 62.2 | 2.7 | 2.8 | 0.7 | 1.5 |
| 7 | 58.5 | 60.5 | 1.7 | 1.7 | 0.1 | 0.5 |
| 8 | Not detected | Not detected | 1.7 | 1.7 | 0.3 | 0.5 |

TABLE 3

| Powder containing Budesonide (HLSA Bud 8%) | |
|---|---|
| Budesonide | 8.0% |
| Leucine | 50.0% |
| Lactose | 41.5% |
| Tween 80 | 0.5% |

TABLE 4

| Powder containing Lactose | | |
|---|---|---|
| Ex. | Respitose SV003 | Lactosphere MM3 |
| 9 | 100.0% | 0.0% |
| 10 | 98.0% | 2.0% |
| 11 | 94.0% | 6.0% |

TABLE 4-continued

Powder containing Lactose

| Ex. | Respitose SV003 | Lactosphere MM3 |
|---|---|---|
| 12 | 91.0% | 9.0% |
| 13 | 90.0% | 10.0% |
| 14 | 85.0% | 15.0% |
| 15 | 80.0% | 20.0% |
| 16 | 70.0% | 30.0% |

TABLE 5

| Ex. | HLSA FF | HLSABDS | Lactose mix from Table 4 |
|---|---|---|---|
| 17 | 0.5% | 2.5% | From example 9 97% |
| 18 | 0.5% | 2.5% | From example 10 97% |
| 19 | 0.5% | 2.5% | From example 11 97% |
| 20 | 0.5% | 2.5% | From example 12 97% |
| 21 | 0.5% | 2.5% | From example 13 97% |
| 22 | 0.5% | 2.5% | From example 14 97% |
| 23 | 0.5% | 2.5% | From example 15 97% |
| 24 | 0.5% | 2.5% | From example 16 97% |

TABLE 6

| Ex. | DF % Formoterol | DF % Budesonide | FPF % Formoterol | FPF % Budesonide |
|---|---|---|---|---|
| 17 | 81.4% | 85.3% | 59.8% | 51.5% |
| 18 | 81.3% | 87.0% | 59.7% | 49.1% |
| 19 | 86.3% | 91.3% | 69.2% | 68.7% |
| 20 | 88.3% | 90.6% | 67.6% | 69.6% |
| 21 | 89.2% | 92.8% | 65.6% | 63.8% |
| 22 | 95.5% | 97.4% | 63.0% | 66.5% |
| 23 | 80.8% | 79.6% | 53.9% | 66.8% |
| 24 | 80.6% | 80.5% | 48.2% | 63.1% |

Example 3

Example 3 was conducted producing formulations containing as active agent Budesonide (defined as HLSA Bud in the table), formulated with lactose and leucine, formulations containing as active agent Formoterol Fumarate (defined as HLSA FF in the table), formulated with lactose and leucine and formulations containing as active agent Tiotropium (defined as HLSA Tio in the table) formulated with lactose and leucine. These formulations were mixed with a lactose powder containing a mixture of Repitose SV003 and of LactoSphere MM3.

Some formulations containing Formoterol and tiotropium at low percentages were also mixed with a powder containing lactose and leucine, in which lactose is used as filler to form a Bulking Agent (defined as BA in the table) or powder containing leucine and lactose but without active agent.

The powders contained in the composition according to the invention are as follows:

TABLE 7

Powder containing Formoterol Fumarate (HLSA FF 2.25%)

| Formoterol Fumarate | 2.25% |
|---|---|
| Leucine | 20.0% |
| Lactose | 77.25% |
| Tween 80 | 0.5% |

TABLE 8

Powder containing Formoterol Fumarate (HLSA FF 4.5%)

| Formoterol Fumarate | 4.5% |
|---|---|
| Leucine | 20.0% |
| Lactose | 75.0% |
| Tween 80 | 0.5% |

TABLE 9

Powder containing Budesonide (HLSA Bud 8%)

| Budesonide | 8.0% |
|---|---|
| Leucine | 50.0% |
| Lactose | 41.5% |
| Tween 80 | 0.5% |

TABLE 10

Powder containing Tiotropium (HLSA Tio 1.5%)

| Tiotropium | 1.5% |
|---|---|
| Leucine | 50.0% |
| Lactose | 48.0% |
| Tween 80 | 0.5% |

TABLE 11

Powder containing Tiotropium (HLSA Tio 3%)

| Tiotropium | 3.0% |
|---|---|
| Leucine | 50.0% |
| Lactose | 46.5% |
| Tween 80 | 0.5% |

TABLE 12

Powder containing Tiotropium (HLSA Tio 6%)

| Tiotropium | 6.0% |
|---|---|
| Leucine | 50.0% |
| Lactose | 43.5% |
| Tween 80 | 0.5% |

TABLE 13

Lactose mix

| Respitose ® SV003 | 91% |
|---|---|
| LactoSphere ® MM3 | 9% |

TABLE 14

| Bulking Agent (BA) | |
|---|---|
| Leucine | 50% |
| Lactose | 49.5% |
| Tween 80 | 0.5% |

The powders were mixed according to the methods described above, in order to obtain formulations containing Budesonide and Formoterol, Tiotropium and mixtures thereof, in a dose of powder of 15 mg.

The parameters evaluated through the MSLI test were the Fine Particle Fraction (FPF %) and the Delivered Fraction (DF %) in conditions with pressure drop of 2 KPa using the inhaler RS01 (Plastiape, Osnago, Lecco,

TABLE 15

| Ex | HLSA FF 2.25% | HLSA FF 4.5% | HLSA Tio 1.5% | HLSA Tio 3% | HLSA Tio 6% | HLSA Bud 8% | BA | Lactose Mix | DF % | FPF % |
|---|---|---|---|---|---|---|---|---|---|---|
| 17 | 0.80% | — | — | — | — | — | — | 99.20% | 87.1% | 40.8% |
| 18 | 0.80% | — | — | — | — | — | 10.00% | 89.20% | 93.3% | 60.4% |
| 19 | 0.80% | — | — | — | — | 8.00% | — | 91.20% | 88.4% | 70.8% |
|  |  |  |  |  |  |  |  |  | Formoterol 89.9% | Formoterol 73.1% |
|  |  |  |  |  |  |  |  |  | Budesonide | Budesonide |
| 20 | — | 0.40% | — | — | — | — | — | 99.60% | 86.4% | 50.5% |
| 21 | — | 0.40% | — | — | — | — | 10.00% | 89.60% | 85.0% | 82.5% |
| 22 | — | — | — | — | — | 8.00% | — | 92.00% | 89.0% | 74.4% |
| 23 | — | — | 2.67% | — | — | — | — | 97.33% | 88.3% | 77.2% |
| 24 | — | — | — | 1.33% | — | — | — | 98.67% | 85.6% | 70.7% |
| 25 | — | — | — | 1.33% | — | — | 10.00% | 88.67% | 93.9% | 79.6% |
| 26 | — | — | — | 1.33% | — | 8.00% | — | 90.67% | 89.2% | 73.3% |
|  |  |  |  |  |  |  |  |  | Tiotropium 93.0% | Tiotropium 74.0% |
|  |  |  |  |  |  |  |  |  | Budesonide | Budesonide |
| 27 | — | — | — | — | 0.67% | — | — | 99.33% | 82.4% | 48.2% |
| 28 | — | — | — | — | 0.67% | — | 10.00% | 89.33% | 92.8% | 69.4% |
| 29 | — | — | — | — | 0.67% | 8.00% | — | 91.33% | 89.2% | 73.3% |
|  |  |  |  |  |  |  |  |  | Tiotropium 93.0% | Tiotropium 74.0% |
|  |  |  |  |  |  |  |  |  | Budesonide | Budesonide |
| 30 | 0.80% | — | — | 1.33% | — | 8.00% | — | 89.87% | 89.9% | 76.2% |
|  |  |  |  |  |  |  |  |  | Tiotropium 95.0% | Tiotropium 76.3% |
|  |  |  |  |  |  |  |  |  | Budesonide 89.8% | Budesonide 74.0% |
|  |  |  |  |  |  |  |  |  | Formoterol | Formoterol |

Example 4

The example was conducted analyzing some products currently on the market containing Formoterol, Budesonide, Tiotropium or combinations thereof (Table 16). Crystalline mixtures of budesonide and formoterol (i.e. not formulated according to the present invention by spray drying) with lactose mixtures with different particle sizes according to the present invention (Table 17A and 17B) were also analyzed.

The products available on the market used for comparison were:

Symbicort® produced by Astrazeneca with Budesonide/Formoterol Fumarate ratio expressed in μg of 160/4.5.

Miflonide®—Budesonide 400 mcg, Novartis Farma S.p.A. —21040 Origgio (VA), Italy

Foradil®—Formoterol Fumarate 12 mcg, Novartis Farma S.p.A.—21040 Origgio (VA), Italy Spiriva®—Tiotropium Bromide, 18 mcg, Boehringer Ingelheim, Italia S.p.A., (MI), Italy The aerodynamic performance of the commercial products was assessed with the MSLI test conducted with a pressure drop of 4 KPa.

The example was conducted in order to assess the aerosol performance of the composition according to the present invention, emphasizing how this composition (see Example 3) can be administered maintaining a high dose of drug delivered through the mouthpiece and a percentage of fine particles able to ensure that the amount of drug deposited in the site of action is capable of performing the correct pharmacological action.

The aerodynamic performance of a dose of 15 mg of each formulation containing crystalline active agents was assessed with the MSLI test conducted at the pressure drop of 2 KPa and 60 l/min.

TABLE 16

|  | FPF % Formoterol | FPF % Budesonide | FPF % Tiotropium |
|---|---|---|---|
| Symbicort® 160/4.5 | 35.6% | 38.4% | — |
| Foradil® | 33.8% | — | — |
| Miflonide® | — | 26.1% | — |
| Spiriva® | — | — | 54.8% |

TABLE 17A

Powder of crystalline Budesonide, Formoterol and Tiotropium

|  | C1 | C2 | C3 | C4 |
|---|---|---|---|---|
| Budesonide Micronized Ph. Eur., Industriale Chimica, S.r.l, Saronno, VA, Italy | 0.64% | 0.64% | — | — |
| Formoterol Fumarate Dihydrate, Ph Eur. 7th Ed., Lusochimica, S.p.A., Lomagna, LC, Italy | 0.018% | — | 0.018% | — |
| Tiotropium Bromide, Euroasian Chemicals PVT LTD, Mumbai - 400001 India | — | — | — | 0.04% |
| Lactose Mix (according to Table XX) | 99.342% | 99.36% | 99.982% | 99.94% |

TABLE 17B

|  | FPF % Formoterol | FPF % Budesonide | FPF % Tiotropium |
|---|---|---|---|
| C1 | 2.1% | 42.8% | — |
| C2 | — | 45.8% | — |
| C3 | 3.7% | — | — |
| C4 | — | — | 1.7% |

The invention claimed is:

1. A pharmaceutical composition for inhalatory use in powder form, which is obtained by preparing:
   a) a first powder comprising at least a powder ($a_1$) comprising an active agent or a pharmaceutically acceptable salt thereof, in an amount greater than 1% by weight of said powder, leucine in amount from 5 to 70% by weight of said powder, a sugar in amount from 20 to 90% by weight of said powder; and
   b) a second powder comprising a mixture of a first lactose which has an X50 from 35 to 75 µm, with a second lactose which has an X50 from 1.5 to 10 µm, the content of said first lactose and second lactose in said mixture being respectively from 85% to 96% and from 4% to 15%,
   c) blending said first powder and said second powder to form a single mixture;
      wherein the ratio by weight of said first powder and said second powder is from 1/5 to 1/100, and said composition has a fine particle fraction (FPF) greater than 60% and a delivered fraction (DF) greater than 80%.

2. The composition according to claim 1, wherein said first powder comprises a third powder ($a_2$) comprising leucine in an amount from 5 to 70% by weight of said third powder and lactose in an amount from 20 to 90% by weight of said third powder.

3. The composition according to claim 1, wherein said first composition comprises an additional powder (a3) comprising an active ingredient or a pharmaceutically acceptable salt thereof, in an amount greater than 1% by weight of said additional powder, leucine in an amount from 5 to 70% by weight of said additional powder, and a sugar in an amount from 20 to 80% by weight of said additional powder.

4. The composition according to claim 1, wherein said active agent is a hydrolyzable active agent.

5. The composition according to claim 1, wherein said active agent is selected from the group consisting of: short and long acting bronchodilator inhalers, corticosteroids, anti-cholinergics, antibiotics, mucolytics, heparin and its derivatives, and substances with antioxidant action.

6. The composition according to claim 1, wherein said sugar is selected from the group consisting of: lactose, trehalose, sucrose and maltodextrin.

7. The composition according to claim 1, wherein said leucine is in an amount from 18 to 55% by weight.

8. The composition according to claim 1, wherein said sugar is in an amount from 40 to 80% by weight.

9. The composition according to claim 1, wherein said powders comprising leucine comprise a surfactant in an amount from 0.2 to 2% by weight of the powder.

10. The composition according to claim 9, wherein said surfactant is selected from the group consisting of benzalkonium chloride, cetrimide, docusate sodium, glyceryl monooleate, sorbitan esters, sodium lauryl sulfate, polysorbates, phospholipids, bile salts, block copolymers of polyoxyethylene and polyoxypropylene.

11. The composition according to claim 9, wherein said surfactant is in an amount from 0.4 to 0.8% by weight.

12. The composition according to claim 1, wherein said first powder has an X50 less than 5 µm.

13. The composition according to claim 1, wherein the content of said first lactose and second lactose in said mixture comprised in said second powder being respectively comprised from 91 to 95% and from 5 to 9%.

14. A kit for the administration of a drug as inhalation powder, comprising a metered amount of the composition according to claim 1 and a device for inhalation.

15. The composition according to claim 2, wherein said first powder comprises an additional powder (a3) comprising an active agent or pharmaceutically acceptable salt thereof, in an amount greater than 1% by weight of said additional powder, leucine in an amount of 5 to 70% by weight of said additional powder, and a sugar in an amount from 20 to 80% by weight of said additional powder.

16. The composition according to claim 2, wherein said active agent is a hydrolyzable active agent.

17. The composition according to claim 3, wherein said active agent of the first powder is a hydrolysable active agent.

18. The composition according to claim 2, wherein said active agent is selected from the group consisting of: short and long acting bronchodilator inhalers, corticosteroids, anti-cholinergics, antibiotics, mucolytics, heparin and its derivatives, substances with antioxidant action.

19. The composition according to claim 3, wherein said active agent of the first powder is selected from the group consisting of: short and long acting bronchodilator inhalers, corticosteroids, anti-cholinergics, antibiotics, mucolytics, heparin and its derivatives, and substances with antioxidant action.

20. The composition according to claim 4, wherein said active agent is selected from the group consisting of: short and long acting bronchodilator inhalers, corticosteroids, anti-cholinergics, antibiotics, mucolytics, heparin and its derivatives, and substances with antioxidant action.

* * * * *